(12) United States Patent
Wu

(10) Patent No.: US 8,926,172 B2
(45) Date of Patent: Jan. 6, 2015

(54) DIFFERENTIAL ADIABATIC COMPENSATION CALORIMETER AND METHODS OF OPERATION

(76) Inventor: Frank Leu Wu, Stafford, TX (US)

(*) Notice: Subject to any disclaimer, the term of this patent is extended or adjusted under 35 U.S.C. 154(b) by 1132 days.

(21) Appl. No.: 12/830,825

(22) Filed: Jul. 6, 2010

(65) Prior Publication Data

US 2011/0007775 A1 Jan. 13, 2011

Related U.S. Application Data

(60) Provisional application No. 61/223,552, filed on Jul. 7, 2009.

(51) Int. Cl.
    *G01K 17/00* (2006.01)
    *G01K 17/04* (2006.01)
    *G01N 25/48* (2006.01)

(52) U.S. Cl.
    CPC ............ *G01K 17/04* (2013.01); *G01N 25/4866* (2013.01)
    USPC .......................................................... 374/34

(58) Field of Classification Search
    USPC .......................................................... 374/34
    See application file for complete search history.

(56) References Cited

U.S. PATENT DOCUMENTS

| | | | | |
|---|---|---|---|---|
| 3,899,918 A | * | 8/1975 | Privalov et al. ................. | 374/11 |
| 4,208,907 A | | 6/1980 | Townsend et al. | |
| 4,439,048 A | | 3/1984 | Townsend et al. | |
| 4,923,306 A | | 5/1990 | Fauske | |
| 5,067,820 A | * | 11/1991 | Donohoue et al. ............. | 374/31 |
| 5,163,753 A | * | 11/1992 | Whiting et al. ................. | 374/10 |
| 5,741,068 A | * | 4/1998 | Hemmerich et al. ........... | 374/31 |
| 5,813,763 A | | 9/1998 | Plotnikov et al. | |
| 6,157,009 A | | 12/2000 | Fauske et al. | |
| 6,530,686 B1 | * | 3/2003 | Nakamura ...................... | 374/11 |
| 6,551,835 B1 | * | 4/2003 | Schawe et al. ................ | 436/147 |
| 7,021,820 B2 | * | 4/2006 | Chippett ......................... | 374/33 |
| 7,476,020 B2 | * | 1/2009 | Zufferey et al. ............... | 374/134 |
| 2004/0014233 A1 | * | 1/2004 | Bannister et al. ............. | 436/155 |
| 2005/0008063 A1 | * | 1/2005 | Chippett ......................... | 374/34 |
| 2008/0025364 A1 | * | 1/2008 | Nakatani et al. ............... | 374/12 |

OTHER PUBLICATIONS

Notification of Transmittal of the International Search Report and the Written Opinion of the International Searching Authority, or the Declaration, International Search Report; and Written Opinion.

* cited by examiner

*Primary Examiner* — Lisa Caputo
*Assistant Examiner* — Jamel Williams
(74) *Attorney, Agent, or Firm* — Novak Druce Connolly Bove + Quigg LLP

(57) ABSTRACT

The differential adiabatic compensation calorimeter comprises sample and reference containers, sample and reference temperature sensors connected back-to-back, in series, sample and reference compensating heaters coupled to the sample and reference containers, and a temperature-controlled chamber. In this differential adiabatic mixing and reaction calorimeter, the sample heat-sink heat loss to the sample container is compensated so that the exothermic reaction is conducted in an adiabatic state, resulting in an undistorted adiabatic process gaining the highest adiabatic temperature rise that corresponds to the theoretical value and an experimentally measured time to maximum rate value. The calorimeter is designed for measuring the time-resolved adiabatic temperature rise, the rate of temperature rise, the time to maximum temperature peak and time to maximum rate of an exothermic chemical reaction.

21 Claims, 4 Drawing Sheets

DIFFERENTIAL ADIABATIC COMPENSATION CALORIMETER AND METHODS OF OPERATION

CROSS-REFERENCE TO RELATED APPLICATIONS

The present application claims priority to U.S. Provisional Patent Application Ser. No. 61/223,552, filed on Jul. 7, 2009, for "A Differential Adiabatic Calorimeter and Methods of Operation."

TECHNICAL FIELD

This invention relates generally to the field of adiabatic calorimeter devices and methods of operation, and more particularly to a differential adiabatic calorimeter using a differential adiabatic compensation technique.

BACKGROUND OF THE INVENTION

Calorimetry is a universal analytical method that measures heat or heat release rate from a biological, chemical or physical sample or process. There are three main categories of calorimeters: temperature scanning calorimeters, isothermal and adiabatic. Differential scanning calorimeter is the most popular temperature scanning calorimeter in which the difference in the form of heat or temperature between the sample and reference is measured as a function of scanned temperature. Differential scanning calorimeters or DSCs use a "dual-cell" design, commonly referred to as a "differential-channel" or "reference-channel" design. This type of "dual-cell" calorimetric design, which consists of a sample channel and a reference channel, is fundamentally different from single channel design in both control and functionality. DSCs have been used widely to study thermophysical or thermochemical properties of materials with a typical sample size in the range of milligrams. Conversely, due to lack of sensitivity, the single-channel scanning calorimeter, i.e., the device without a reference channel, is not popular and mostly used for rough screening purpose. One of the major disadvantages of temperature scanning calorimetry is that the time-resolved thermochemical information cannot be experimentally obtained.

Isothermal calorimeters are used mainly for monitoring time-resolved reaction processes, because many of the desired manufacturing processes in the chemical and pharmaceutical industry are isothermal. While liter-scale reactions are normally tested on single channel isothermal reaction calorimeters, gram-scale reaction calorimetric studies are typically performed on isothermal microcalorimeters (e.g., SuperCRC™ isothermal reaction microcalorimeter) using the differential or referencing calorimetric design principle similar to that of DSCs.

Adiabatic calorimetry has been also used for physical property measurement (e.g., specific heat and phase transfer studies) and reaction process monitoring (e.g., chemical reaction upon mixing or decomposition upon temperature rise). More recently, adiabatic calorimeters have been used to measure temperature and pressure as a function of time in order to look at undesired chemical reactions. When chemical mixing, reaction or decomposition becomes exothermic, the heat released from the sample may cause a significant temperature excursion, and sometimes develop into a self-perpetuated, thermal runaway reaction. Current adiabatic calorimeters are all single channel devices.

To study this self-perpetuating reaction, an adiabatic calorimeter, called the accelerating rate calorimeter (ARC), was developed (U.S. Pat. No. 4,208,907). However, this single-channel calorimeter is a quasi-adiabatic device, since a large portion of the heat released by sample is absorbed by or sinks to the sample container. Because this heat sink effect, the experimental temperature rise and the rate of temperature rise are, therefore, dampened or lower than the theoretical limits, causing a so-called "thermal lag" effect that significantly slows down the reaction progress and results in an erroneous time to maximum rate (TMR), a critical value in runaway reaction hazard assessment. Another single-channel adiabatic calorimeter with a compensation approach was also developed (U.S. Pat. No. 4,130,016), with the idea that the heat-sink heat loss could be compensated by using a compensation heater which is attached to the outer wall of the sample container. However not only did the device fail to deliver a calorimetric result better than 95%, it also is difficult to downsize this liter-scale container to meet the analytical lab standards, and therefore has never been commercialized.

Since the early 2000s, some single-channel scanning calorimeter devices were developed in order to reduce the container heat-sink effect and reach a higher adiabaticity (U.S. Pat. No. 6,157,009 and No. 7,021,820). However, these scanning devices are neither adiabatic nor isothermal, therefore, the time-resolved temperature and pressure information, such as the maximum adiabatic temperature rise and time to maximum rate (TMR), can't be measured on these devices.

Although the differential compensation principle has been used in the instrument design of several commercial isothermal and DSC calorimeters, it has never been used in adiabatic calorimetry. In contrast to prior quasi-adiabatic calorimeters, the present invention is a differential compensation adiabatic calorimeter, which is a unique instrument in the field of calorimetry. In this true adiabatic mixing and reaction calorimeter, the sample heat-sink heat loss to the sample container can be fully compensated so that the reaction can be conducted in a truly adiabatic state. The differential adiabatic compensation feedback circuit guaranties that neither under- nor over-compensation is made, 100% adiabaticity is achieved, the maximum temperature rise, time to peak temperature and time to maximum rate all can be experimentally measured without thermal lag.

SUMMARY OF THE INVENTION

The present invention includes a novel differential adiabatic compensation calorimeter and methods of operation for the new calorimeter. The differential adiabatic compensation calorimeter disclosed herein is designed for measuring the time-resolved adiabatic temperature rise, the rate of temperature rise, the time to maximum temperature peak and time to maximum rate of an exothermic chemical reaction. By measuring the temperature difference between the sample and reference containers and using the differential adiabatic heat compensating technique of this invention, the heat absorbed by or sunk to the sample container is completely compensated in real-time, resulting in an undistorted, true adiabatic process gaining both the highest time-resolved adiabatic temperature rise that matches the theoretical value, and an experimentally measured true adiabatic time to maximum rate ($TMR_{ad}$) value. Also, due to the elimination of container heat sink effect, chemically dilute samples or samples with low exothermic activities can now be tested on this differential adiabatic compensation calorimeter.

The basic calorimeter comprises sample and reference containers, sample and reference temperature sensors, sample and reference compensating heaters coupled to the sample and reference containers, a heat compensation system, a temperature-controlled chamber disposed around the sample and reference containers and a chamber-temperature-control system. In this new differential adiabatic compensation calorimeter, the compensating heat is applied to both sample and reference containers by the sample and reference compensation heaters, respectively, before and throughout the entire exothermic event. This differential adiabatic compensation calorimeter may be used as a general thermal analytical tool for various calorimetric applications, including but not limited to, mixing calorimetry, self-heat rate, temperature rise, and time to maximum rate measurements.

The calorimetric operation is initiated by heating the sample to the desired temperature, starting the compensation heating control, injecting and mixing a second sample if needed, and searching for an exothermic activity. When the exothermic activity occurs and a temperature difference between the sample and reference is detected, the heat output of the sample and reference heater are adjusted such that the temperature difference is returned to zero by a differential heat compensating circuit. The temperature difference between the sample and reference containers, which is proportional to the sample heat absorbed by the sample container, is measured by back-to-back connected sample and reference temperature sensors. The temperature of the adiabatic chamber is also increased in order to maintain adiabatic conditions around the sample and reference containers, and the sample temperature is allowed to accelerate adiabatically to a maximum.

The present invention, which has been proven in theory and practice, creates a so-called "containerless" effect that results in total heat loss compensation, i.e., the sample does not gain or lose heat to the sample container. The advantage of the "containerless" effect is that experiments can be carried out in real-world chemical process conditions, and parameters obtained are readily scalable (i.e., instrument-independent). Theoretical time-temperature and time-pressure rises and rates can be obtained experimentally.

In contrast to prior heat compensation calorimeters in which the compensational heating power or heating power difference supplied by the heating devices to the sample system constitutes the measured magnitude, no compensational heating power or heating power difference is ever needed and recorded by this differential adiabatic compensation calorimeter.

An additional advantage of the differential adiabatic compensation technique over other compensation techniques is that, since the temperature difference between the sample and reference containers is the only compensation feedback control parameter, the heat capacities and masses of the sample and containers become all irrelevant values for heating control and result calculation. This special instrument feature simplifies the testing procedures and eliminates control errors caused by the uncertainty in the estimated container heat capacity value.

Still, other objects, features, and advantages of the present invention will be apparent from the following description of the preferred embodiments, given for the purpose of disclosure, and taken in conjunction with the accompanying drawings and figures.

BRIEF DESCRIPTION OF THE FIGURES

For a further understanding of the nature and objects of the present inventions, reference should be made to the following detailed disclosure, taken in conjunction with the accompanying drawings, in which like parts are given like reference numerals, and wherein.

DETAILED DESCRIPTION OF PREFERRED EMBODIMENTS OF THE INVENTIONS

Figure 1:
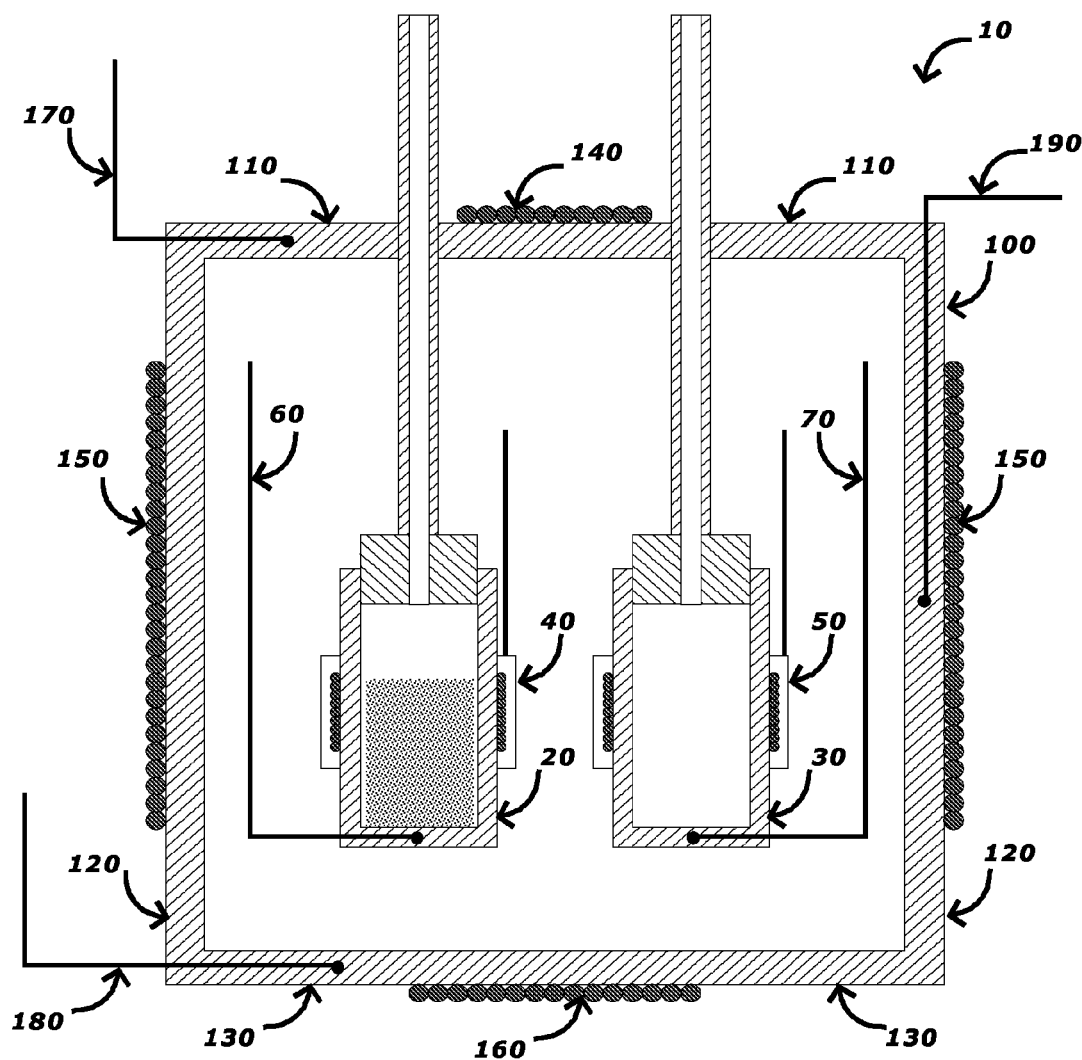
FIG. 1 is a cross-sectional view of an embodiment of the invented differential adiabatic compensation calorimeter.

A cross-sectional view of an embodiment of a differential adiabatic compensation calorimeter is shown in FIG. 1. As shown in FIG. 1, the calorimeter 10 comprises: a sample container 20, a reference container 30; a heat compensation control system, and an adiabatic chamber 100 disposed around the sample container 20 and the reference container 30, and a chamber temperature control system. In a preferred embodiment, the sample container 20 and the reference container 30 have an identical construction to minimize any differences in their thermal behavior.

In an embodiment, the sample container 20 is disposed within an adiabatic chamber 100. The sample container 20 may be made from any suitable materials for the desired sample conditions (e.g., temperature, pressure, chemical composition, etc.). Suitable materials for the sample container 20 include, but are not limited to, various metals such as stainless steels, titanium alloys, Monel™ alloys, Hastelloy C™ alloys and combinations thereof. The sample container 20 is adapted to receive and contain a reactive chemical sample as is commonly known to those skilled in the art. In a preferred embodiment, the sample container 20 is closed during operation of the calorimeter.

In an embodiment, the reference container 30 is disposed within an adiabatic chamber 100. The reference container 30 may be made from any suitable materials for the desired conditions (e.g., temperature, pressure, reference chemical composition, etc.). Suitable materials for the sample container 20 include, but are not limited to, various metals such as stainless steels, titanium alloys, Monel™ alloys, Hastelloy C™ alloys and combinations thereof. In a preferred embodiment, the reference container 30 is made from the same materials as the sample container 20 to minimize any differences in their thermal behavior. In a preferred embodiment, the reference container 30 is adapted to receive and contain a solvent or nothing. In a preferred embodiment, the reference container 30 is closed during operation of the calorimeter.

The heat compensation control system comprises: a sample compensation heater 40, wherein the sample compensation heater 40 is coupled to the sample container 20; a sample temperature sensor 60, wherein the sample temperature sensor 60 is coupled to the sample container 20; a reference compensation heater 50, wherein the reference compensation heater 50 is coupled to the reference container 30; a reference temperature sensor 70, wherein the reference temperature sensor 70 is coupled to the reference container 30.

The sample compensation heater 40 includes any suitable heater technology. In an embodiment, the sample compensation heater 40 includes an AC or DC band heater, silicon rubber heater. In a preferred embodiment, the sample compensation heater 40 is a light-weight differential compensation heater. The sample compensation heater 40 may be attached to the sample container 20 using any means appropriate for the specific heater. In a preferred embodiment, the sample compensation heater 40 may be coupled to the outside surface of the sample container 20. For example, a band heater may be clamped to the outer surface of the sample container 20, and a silicon rubber heater may be glued to the outer surface using an adhesive recommended by the heater manufacturer.

A sample temperature sensor 60 includes any suitable thermal sensing technology. In an embodiment, the sample temperature sensor 60 may be a platinum resistance thermometer (PRT). In a preferred embodiment, the sample temperature sensor 60 is a sheathed thermocouple (TC). The sensing portion of the temperature sensor 60 is positioned to contact a surface of the sample container 20. In a preferred embodiment, the sample temperature sensor 60 may be coupled to an outside surface of the sample container 20. In a preferred embodiment, the sensing portion may be inserted into a channel drilled for the sensor 60. The temperature sensor 60 may be held in place with any number of conventional fasteners, brackets, clamps or set screws.

In an embodiment, the sample compensation heater 40 and the sample temperature sensor 60 may be separated and coupled to different surfaces of the sample container 20.

The reference compensation heater 50 includes any suitable heater technology. In an embodiment, the reference compensation heater 50 includes an AC or DC band heater, silicon rubber heater. In a preferred embodiment, the reference compensation heater 50 is a light-weight differential compensation heater. The reference compensation heater 50 may be attached to the reference container 30 using any means appropriate for the specific heater. In a preferred embodiment, the reference compensation heater 50 may be coupled to the outside surface of the reference container 30. For example, a band heater may be clamped to the outer surface of the reference container 30, and a silicon rubber heater may be glued to the outer surface using an adhesive recommended by the heater manufacturer.

A reference temperature sensor 70 includes any suitable thermal sensing technology. In an embodiment, the reference temperature sensor 70 may be a platinum resistance thermometer (PRT). In a preferred embodiment, the reference temperature sensor 70 is sheathed thermocouple (TC). In a preferred embodiment, the reference temperature sensor 70 is the same type of sensor as the sample temperature sensor 60 to minimize the differences between the sample container 20 and the reference container 30. The sensing portion of the reference temperature sensor 70 is positioned to contact a surface of the reference container 30. In a preferred embodiment, the reference temperature sensor 70 may be coupled to an outside surface of the reference container 30. In a preferred embodiment, the sensing portion is inserted into a channel drilled for the sensor 70. The temperature sensor 70 may be held in place with any number of conventional fasteners, brackets, clamps or set screws. In a preferred embodiment, the reference temperature sensor 70 is back-to-back connected in series with the sample temperature sensor 60.

In an embodiment, the reference compensation heater 50 and the reference temperature sensor 70 may be separated and coupled to different surfaces of the reference container 30. In a preferred embodiment, the reference temperature sensor 70 is located in the same relative position of the reference container 30 as the sample temperature sensor 60 is located in the sample container 20 to minimize any difference in their thermal behavior.

Figure 2:
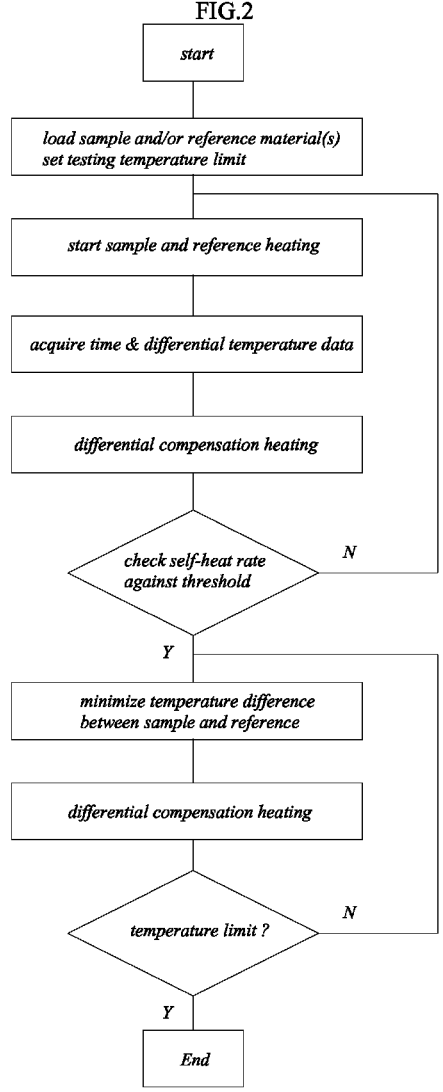
FIG. 2 is a schematic drawing illustrating the differential compensation control system of the invented differential adiabatic compensation calorimeter in FIG. 1.

A temperature-compensation-control system for the differential adiabatic calorimeter is shown schematically in FIG. 2. At the start of a temperature-compensation-control sequence, the temperature of the sample container 20 and the temperature of the reference container 30 are measured by the sample temperature sensor 60 and the reference temperature sensor 70, respectively. In a preferred embodiment, a closed-loop, differential heat compensation system monitors the sample temperature sensor 60 and the reference temperature sensor 70, and controls the sample compensation heater 40 and the reference compensation heater 50. Compensating heat is added to the sample container 20 by the sample compensation heater 40. The same amount of heat is also added to the reference container 30 by the reference compensation heater 50. The temperature difference between the sample container 20 and the reference container 30 is minimized by adding heat to the sample container 20 by the sample compensation heater 40 and to the reference container 30 by the reference compensation heater 50. The adiabatic sample self-heat rate of an exothermic reaction is checked against an instrumental threshold value, normally set at about 0.02° C./min. When the self-heat rate occurs and a temperature difference between the sample container 20 and the reference container 30 is detected, the adiabatic self-heat rate is allowed to accelerate to a maximum.

In an embodiment, a method of differential compensation control for the differential adiabatic calorimeter comprises the steps of: measuring a temperature difference between a sample container 20 and a reference container 30 as measured by a sample temperature sensor 60 and a reference temperature sensor 70; minimizing the temperature difference between the sample container 20 and the reference container 30 by controlling a sample compensation heater 40 and a reference compensation heater 50; and controlling the sample compensation heater 40 and the reference compensation heater 50 by adding an amount of heat to the sample container 20 by the sample compensation heater 40 and another amount of heat to the reference container 30 by the reference compensation heater 50.

Referring to FIG. 1, a chamber 100 comprises a top plate 110, a side wall 120 and a bottom plate 130. The top plate 110, side wall 120 and bottom plate 130 are disposed around the sample container 20 and the reference container 30. The top plate 110, the side wall 120 and the bottom plate 130 may be made of any suitable material for the desired temperature range. The outer surface of the adiabatic chamber 100 is covered with a layer of insulation. The insulation includes any suitable high efficiency insulation materials for the desired temperature range. In a preferred embodiment, the insulation material is a high temperature insulation material. In a preferred embodiment, the chamber 100 is closed during operation of the calorimeter.

The chamber-temperature-control system comprises: a top plate heater 140 coupled to the top plate 110, a top plate temperature sensor 170 coupled to the top plate 110; a side wall heater 150 coupled to the side wall 120; a side wall temperature sensor 180 coupled to the side wall 120; a bottom plate heater 160 coupled to the bottom plate 130; a bottom plate temperature sensor 190 coupled to the bottom plate 130, wherein the chamber-temperature-control system controls the temperature of the top plate 110, the side wall 120 and the bottom plate 130 individually to achieve a uniform temperature inside the chamber 100.

The top plate heater 140, the side wall heater 150 and the bottom plate heater 160 includes any suitable heater technology. In an embodiment, the top plate heater 140, the side wall heater 150 and the bottom plate heater 160 includes an AC or DC band heater and a silicon rubber heater. The top plate heater 140, the side wall heater 150 and the bottom plate heater 160 may be attached to the top plate 110, the side wall 120 and the bottom plate 130, respectively, using any means appropriate for the specific heater. In a preferred embodiment, the top plate heater 140, the side wall heater 150 and the bottom plate heater 160 may be attached to an outside surface of the top plate 110, the side wall 120 and the bottom plate 130, respectively. For example, a band heater may be clamped to an outer surface, and a silicon rubber heater may be glued to the outer surface using an adhesive recommended by the heater manufacturer.

The top plate temperature sensor 170, the side wall temperature sensor 180 and the bottom plate temperature sensor 190 include any suitable thermal sensing technology, as discussed above. In a preferred embodiment, the top plate temperature sensor 170, the side wall temperature sensor 180 and the bottom plate temperature sensor 190 includes a platinum resistance thermometer (PRT). The sensing portions of the top plate temperature sensor 170, the side wall temperature sensor 180 and the bottom plate temperature sensor 190 are coupled to the top plate 110, the side wall 120 and the bottom plate 130, respectively. In a preferred embodiment, the sensing portions of the top plate sensor 170, the side wall sensor 180 and the bottom plate sensor 190 are coupled an outside surface of the top plate 110, the side wall 120 and the bottom plate 130, respectively. In a preferred embodiment, the sensing portion is inserted into a channel drilled for the sensor. The top plate temperature sensor 170, the side wall temperature sensor 180 and the bottom plate temperature sensor 190 may be held in place with any number of conventional fasteners, brackets or clamps.

In a preferred embodiment, the heat-compensation-control system and the chamber-temperature-control system are connected to a computer system. In a preferred embodiment, the computer records the temperatures associated with the sample temperature sensor 60, the reference temperature sensor 70 and the chamber temperature sensors 170, 180 and 190 as functions of time. In a preferred embodiment, the computer regulates the amount of heat loss of a sample to the sample container 20 to be input into the sample container 20 by the compensation heater 40.

Generally, the operation of the calorimeter 10 is initiated by loading a reactive chemical sample into the sample container 20, and followed by raising the temperature of the sample container 20 and reference container 30, and searching for the detection of an adiabatic sample self-heat rate of an exothermic reaction by the instrument, as described above. When the self-heat rate is detected, the exothermic reaction is allowed to accelerate to a maximum. During the self-heating period, any difference in temperature between the sample container 20 and the reference container 30 as measured by the sample temperature sensor 60 and the reference temperature sensor 70 is recorded as a function of time. In a preferred embodiment, the amount of heat absorbed by the sample container 20 is proportional to the temperature difference between the sample and reference, and input back into the sample container 20 by the sample compensation heater 40. In a preferred embodiment, the same amount of heat is also input into the reference container 30 by the reference compensation heater 50. The temperature of the adiabatic chamber 100 is also increased in order to maintain adiabatic conditions around the sample container 20 and the reference container 30.

Figure 3:
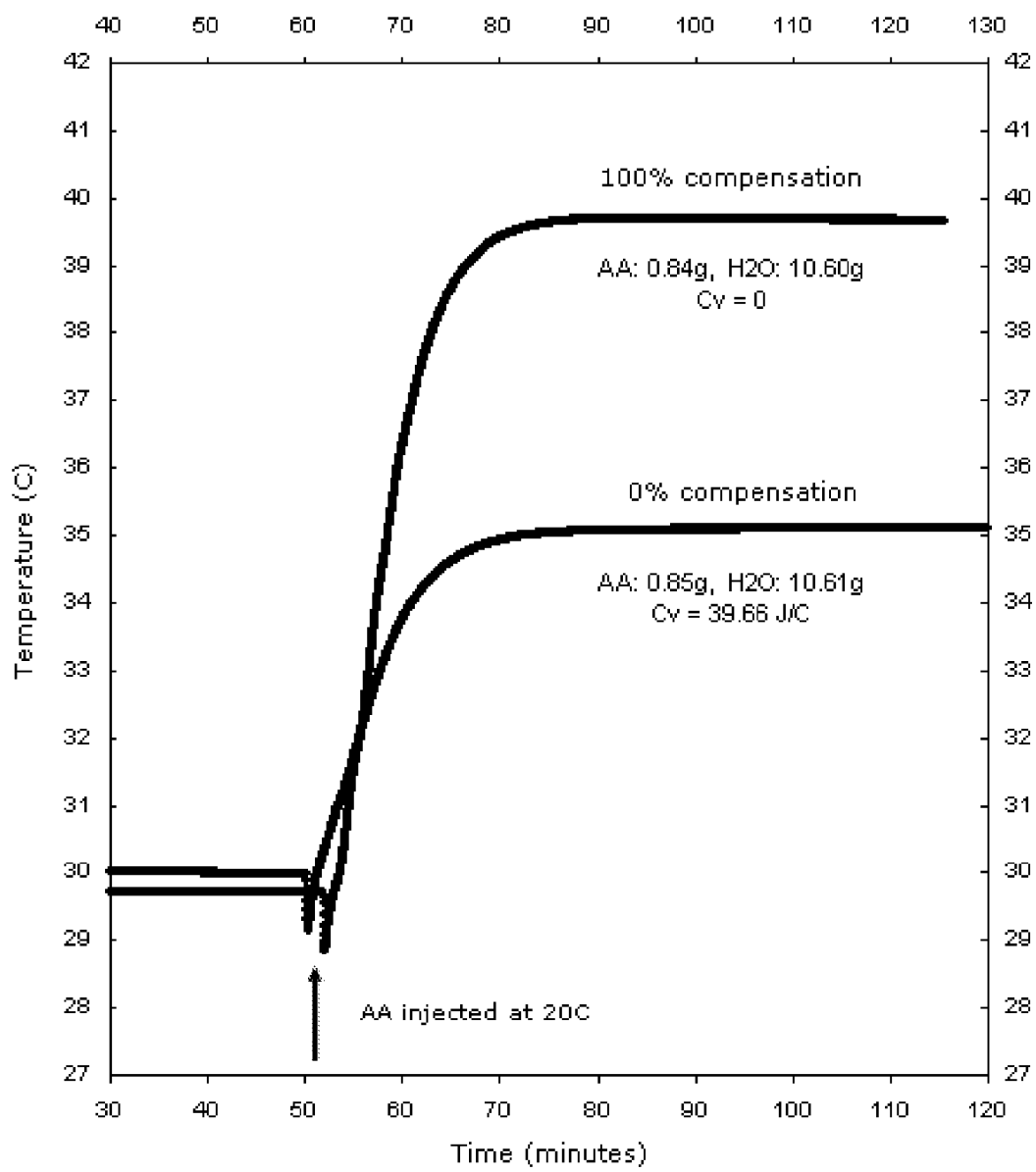
FIG. 3 shows an adiabatic mixing calorimetric experiment of the temperature rise measurement of acetic anhydride hydrolysis reaction with and without differential adiabatic compensation.
Figure 4:
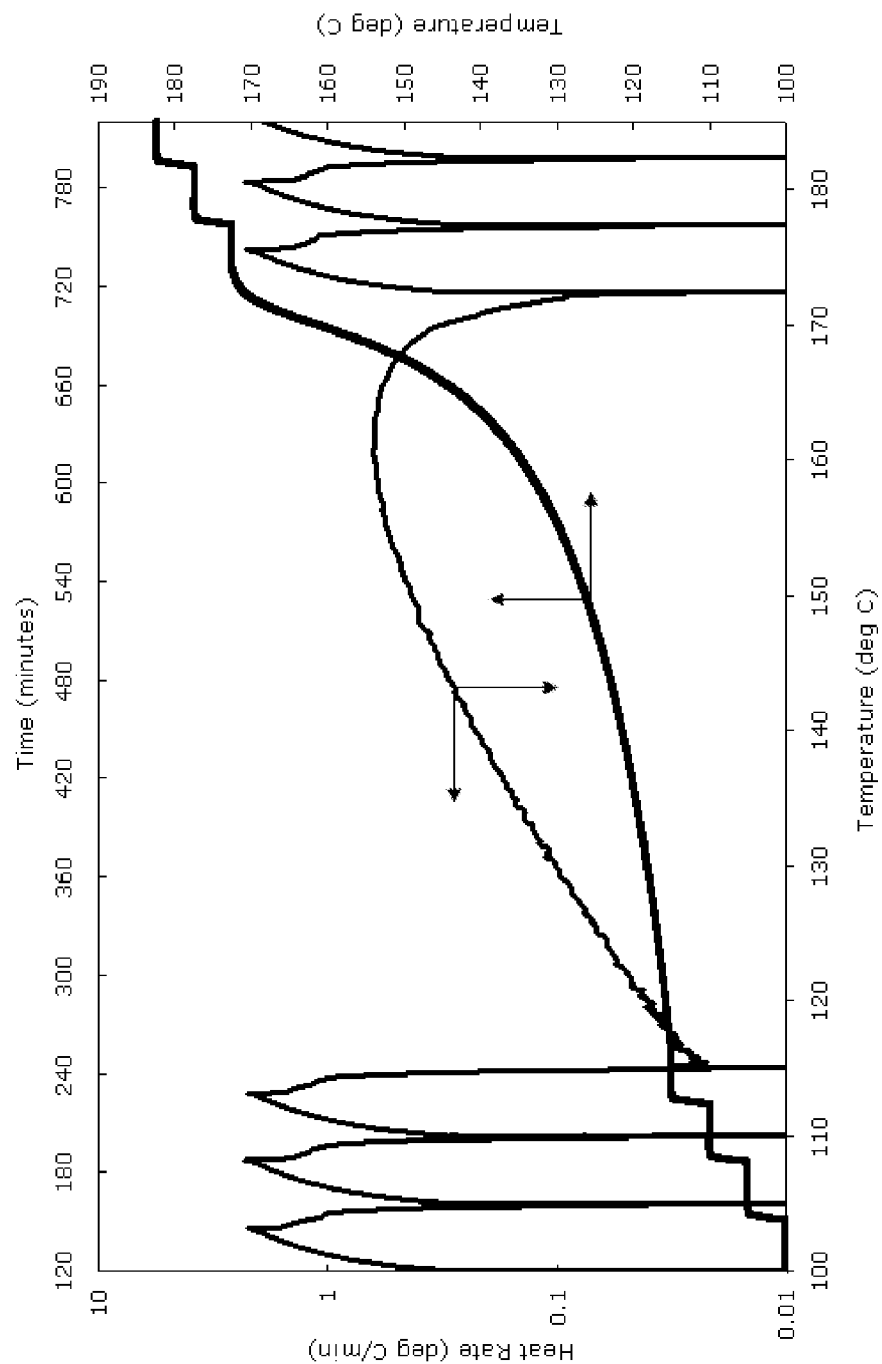
FIG. 4 shows a time-resolved differential adiabatic temperature tracking experiment of the exothermic di-tertiary-butyl-peroxide (DTBP) decomposition with differential adiabatic compensation.

In an embodiment, a method of operation to determine the time-resolved temperature rise of an exothermic chemical reaction comprising of the steps: placing a sample in a sample container 20, and a solvent or nothing in a reference container 30; measuring a time-resolved temperature rise of an exothermic activity of the sample; heating the sample container 20 and the reference container 30 by a sample compensation heater 40 and a reference compensation heater 50 to an isothermal temperature and controlling the containers 20, 30 at that temperature until a self-heating activity is detected, or a second sample is injected and mixed; when the self-heating activity is detected, allowing the exothermic activity to go to completion adiabatically; during the self-heating step, adjusting the heat output of the sample compensation heater 40 and the heat output of the reference compensation heater 50, to minimize the temperature difference between the sample container 20 and reference container 30 as measured by the sample temperature sensor 60 and the reference temperature sensor 70, wherein the sample compensation heater 40 provides only enough heat output to compensate for the sample heat-sink heat loss to the sample container 20, and the reference compensation heater 50 provides only enough heat output to the reference container 30 in order to minimize the temperature difference between the sample container 20 and the reference container 30. In an embodiment the method further comprises the step of: determining the time to maximum rate and the maximum temperature rise for the exothermic activity of the sample, as shown in FIGS. 3 and 4.

In an embodiment, the temperature difference between the sample container 20 and the reference container 30 may be minimized such that mass and heat capacity information for the sample and sample container 20 are not required for controlling sample temperature and compensation heating. In an embodiment, the sample compensation heater 40 and the sample temperature sensor 60 may be separated and coupled to different surfaces of the sample container 20. Similarly, the reference compensation heater 50 and the reference temperature sensor 70 may be separated and coupled to different surfaces of the reference container 30.

In another embodiment, a method of operation to determine the temperature rise rate of an exothermic chemical reaction comprises the steps: placing a sample in a sample container 20, and a solvent or nothing in a reference container 30; heating the sample container 20 and the reference container 30 by a sample compensation heater 40 and a reference compensation heater 50 to a temperature at which a self-heating activity is detected; when the self-heating activity is detected, allowing the exothermic activity of the sample to go completion exponentially and adiabatically; during the self-heating step, providing only enough heat output to compensate for the sample heat-sink heat loss to the sample container 20 by the sample compensation heater 40; and providing only enough heat output to the reference container 30 in order to minimize the temperature difference between the sample container 20 and reference container 30 by the reference compensation heater 50; and during the heating and the self-heating steps, adjusting the heat output of the sample compensation heater 40 and the heat output of the reference compensation heater 50, to minimize the temperature difference between the sample container 20 and the reference container 30 as measured by the sample temperature sensor 60 and the reference temperature sensor 70. In an embodiment, the method further comprises the step of determining a maximum temperature rise for the exothermic activity of the sample, as shown in FIG. 4.

In another embodiment, the temperature difference between the sample container 20 and the reference container 30 may be minimized such that mass and heat capacity information for the sample and sample container 20 are not required for controlling temperature and compensation heating. In an embodiment, the sample compensation heater 40 and the sample temperature sensor 60 may be separated and coupled to different surfaces of the sample container 20. Similarly, the reference compensation heater 50 and the reference temperature sensor 70 may be separated and coupled to different surfaces of the reference container 30.

Mixing Calorimetry Example

The new differential adiabatic compensation calorimeter may be used as mixing calorimeter as shown in FIG. 3. As shown in FIG. 3, experimental data was obtained from an adiabatic mixing calorimetric experiment of the temperature rise measurement of acetic anhydride hydrolysis reaction with and without differential adiabatic compensation. For the 100% compensation experiment, 0.84 grams of acetic anhydride was injected at 20° C. into 10.60 grams of water, and, for the 0% compensated experiment, 0.85 grams of acetic anhydride was injected at 20° C. into 10.61 grams of water.

With the 100% adiabaticity in the new calorimeter, the maximum temperature rise and energy release due to the mixing or interacting of the chemicals was experimentally obtained, as shown in FIG. 3. Importantly, the new calorimeter was used as a time-temperature measurement device. This experiment demonstrates that the new calorimeter may be used as a mixing calorimeter, similar to, but without the short comings of, a Dewar calorimeter.

Temperature Tracking Calorimetry Example

The new calorimeter may be used as a temperature tracking calorimeter as shown in FIG. 4. As shown in FIG. 4, experimental data was obtained for a time-resolved differential adiabatic temperature tracking experiment of the exothermic di-tertiary-butyl-peroxide (DTBP) decomposition with differential adiabatic compensation. A solution of 8 wt % DTBP in toluene was used in the experiment.

With 100% adiabaticity and zero thermal lag in the new calorimeter, the time-resolved temperature information, adiabatic temperature rise, self-heating temperature rates, and adiabatic time to maximum temperature rate value ($TMR_{ad}$) were all be experimentally measured, as shown in FIG. 4. This experiment demonstrates that the new calorimeter may be used as temperature tracking calorimeter, similar to, but without the deficiencies of, the single-channel ARC calorimeter.

Definitions

As used herein, the terms "a," "an," "the," and "said" means one or more. As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone: A and B in combination; A and C in combination; B and C in combination; or A, B, and C in combination.

As used herein, the terms "comprising," "comprises," and "comprise" are open-ended transition terms used to transition from a subject recited before the term to one or elements recited after the term, where the element or elements listed after the transition term are not necessarily the only elements that make up of the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the term "simultaneously" means occurring at the same time or about the same time, including concurrently.

Incorporation By Reference

All patents and patent applications, articles, reports, and other documents cited herein are fully incorporated by reference to the extent they are not inconsistent with this invention.

What is claimed is:

1. A differential adiabatic compensation calorimeter for measuring the true adiabatic temperature rise and the time to maximum rate of an exothermic reaction, the calorimeter comprising:
   a) a sample container disposed within a temperature-controlled chamber, wherein the sample container is adapted to receive a sample;
   b) a reference container disposed within the temperature-controlled chamber, wherein the reference container is adapted to receive a solvent or nothing;
   c) a heat-compensation-control system comprising:
      i. a sample compensation heater coupled to the sample container;
      ii. a reference compensation heater coupled to the reference container;
      iii. a sample temperature sensor coupled to the sample container;
      iv. a reference temperature sensor coupled to the reference container; and
      v. wherein the heat-compensation-control system is configured to:
         control a heat output to the sample compensation heater and a heat output to the reference compensation heater to minimize the temperature difference between the sample container and the reference container;
         detect self-heating activity of the sample in reference to a predetermined instrumental threshold value, and upon such detection, allow the exothermic reaction to accelerate to completion adiabatically;
         detect self-heating activity of the sample in combination with a second sample after an injection and mixing of the second sample within the sample container in reference to a predetermined instrumental threshold value, and upon such detection, allow the exothermic reaction to accelerate to completion adiabatically.

2. The calorimeter of claim 1, wherein the reference temperature sensor is connected to the sample temperature sensor.

3. The calorimeter of claim 1, wherein the temperature-controlled chamber comprises:
   a) a top plate;
   b) a side wall; and
   c) a bottom plate.

4. The calorimeter of claim 3, wherein the temperature-controlled chamber further comprises:
   a) a chamber-temperature-control system comprising:
      i. a top plate heater coupled to the top plate,
      ii. a top plate temperature sensor coupled to the top plate heater, wherein the top plate temperature sensor is connected to the chamber-temperature-control system;
      iii. a side wall heater coupled to the side wall;
      iv. a side wall temperature sensor coupled to the side wall heater, wherein the side wall temperature sensor is connected to the chamber-temperature-control system;
      v. a bottom plate heater coupled to the bottom plate;

vi. a bottom plate temperature sensor coupled to the bottom plate heater, wherein the bottom plate temperature sensor is connected to the chamber-temperature-control system; and vii. wherein the chamber-temperature-control system controls the temperature of the top plate, the side wall and the bottom plate to achieve a uniform temperature inside the chamber.

5. The calorimeter of claim 1, wherein the reference container is positioned symmetrically to the sample container within the temperature-controlled chamber.

6. The calorimeter of claim 1, wherein the sample container and the reference container are made from the group consisting of stainless steels, titanium alloys, Monel alloys, Hastalloy C alloys and combination thereof.

7. The calorimeter of claim 1, wherein the sample compensation heater and the reference compensation heater are controlled simultaneously.

8. The calorimeter of claim 4, wherein the top plate, the side wall and the bottom plate are controlled individually.

9. The calorimeter of claim 1, wherein the sample compensation heater and the sample temperature sensor are separated and coupled to different surfaces of the sample container.

10. The calorimeter of claim 1, wherein the reference compensation heater and the reference temperature sensor are separated and coupled to different surfaces of the reference container.

11. The calorimeter of claim 1, wherein the reference temperature sensor is back-to-back connected in series with the sample temperature sensor.

12. The calorimeter of claim 1, wherein the temperature-controlled chamber is closed.

13. A method of differential compensation control for the calorimeter of claim 1, the method comprising:
  a) measuring a temperature difference between a sample container and a reference container as measured by a sample temperature sensor and a reference temperature sensor;
  b) minimizing the temperature difference between the sample container and the reference container by controlling a sample compensation heater and a reference compensation heater; and
  c) controlling the sample compensation heater and the reference compensation heater by adding an amount of heat to the sample container by the sample compensation heater and another amount of heat to the reference container by the reference compensation heater.

14. A method of operation for the calorimeter of claim 1 to determine the time-resolved temperature rise of an exothermic chemical reaction, the method comprising:
  a) placing a sample in a sample container, and a solvent or nothing in a reference container;
  b) measuring a time-resolved temperature rise of an exothermic activity of the sample;
  c) heating the sample container and the reference containers by a sample compensation heater and a reference compensation heater to an isothermal temperature and controlling the containers at that temperature until a self-heating activity is detected or a second sample is injected and mixed;
  d) when self-heating activity is detected, allowing the exothermic activity to accelerate to completion adiabatically;
  e) during the self-heating step, adjusting the heat output of the sample compensation heater and the heat output of the reference compensation heater, to minimize the temperature difference between the sample container and reference container as measured by the sample temperature sensor and the reference temperature sensor, wherein the sample compensation heater provides only enough heat output to compensate for the sample heat-sink heat loss to the sample container, and the reference compensation heater provides only enough heat output to the reference container to minimize the temperature difference between the sample container and reference container.

15. The method of claim 14, further comprising the step of determining the time to maximum rate and the maximum temperature rise for the exothermic activity of the sample.

16. The method of claim 14, wherein the temperature difference between the sample container and the reference container is minimized such that mass and heat capacity information for the sample and sample container are not required for controlling sample temperature and compensation heating.

17. A method of operation for the device of claim 1 to determine the temperature rise rate of an exothermic chemical reaction, the method comprising:
  a) placing a sample in a sample container, and a solvent or nothing in a reference container;
  b) heating the sample container and the reference container by a sample compensation heater and a reference compensation heater to a temperature at which a self-heating activity is detected;
  c) when self-heating activity is detected, allowing the exothermic activity of the sample to accelerate to completion exponentially and adiabatically;
  d) during the self-heating step, providing only enough heat output to compensate for the sample heat-sink heat loss to the sample container by the sample compensation heater; and
  providing only enough heat output to the reference container to minimize the temperature difference between the sample container and the reference container by the reference compensation heater; and
  e) during the heating and the self-heating steps, adjusting the heat output of the sample compensation heater and the heat output of the reference compensation heater, to minimize the temperature difference between the sample container and the reference container as measured by the sample temperature sensor and the reference temperature sensor.

18. The method of claim 17, further comprising the step of determining a maximum temperature rise for the exothermic activity of the sample.

19. The method of claim 17, wherein the temperature difference between the sample container and the reference container is minimized such that mass and heat capacity information for the sample and sample container are not required for controlling sample temperature and compensation heating.

20. The method of claim 17, wherein the sample compensation heater and the sample temperature sensor are separated and coupled to different surfaces of the sample container.

21. The method of claim 17, wherein the reference compensation heater and the reference temperature sensor are separated and coupled to different surfaces of the reference container.

* * * * *